(12) United States Patent
Kurris et al.

(10) Patent No.: US 9,272,085 B2
(45) Date of Patent: Mar. 1, 2016

(54) METHOD OF INTRODUCING A CATHETER (71) Applicants: Michael R. Kurris, Ellettsville, IN (US);
Katherine McKrill, Bloomington, IN (US)

(72) Inventors: Michael R. Kurris, Ellettsville, IN (US);
Katherine McKrill, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 405 days.

(21) Appl. No.: 13/761,664

(22) Filed: Feb. 7, 2013

(65) Prior Publication Data

US 2014/0221831 A1 Aug. 7, 2014

Related U.S. Application Data

(62) Division of application No. 12/849,501, filed on Aug. 3, 2010, now abandoned.

(51) Int. Cl.
*A61M 25/00* (2006.01)
*A61M 5/00* (2006.01)
*A61M 25/06* (2006.01)
*A61M 29/00* (2006.01)

(52) U.S. Cl.
CPC ............ *A61M 5/007* (2013.01); *A61M 25/0662* (2013.01); *A61M 25/0668* (2013.01); *A61M 29/00* (2013.01); *A61M 2025/0681* (2013.01)

(58) Field of Classification Search
CPC ...................... A61M 25/0662; A61M 25/0668; A61M 29/00; A61M 2025/0681; A61M 5/007
See application file for complete search history.

(56) References Cited

U.S. PATENT DOCUMENTS 3,670,729 A * 6/1972 Bennett et al. ................ 604/500
RE31,855 E 3/1985 Osborne
4,629,450 A 12/1986 Suzuki et al.
(Continued)

FOREIGN PATENT DOCUMENTS

DE 198 16 986 C1 8/1999
EP 0 555 088 A2 8/1993
(Continued)

OTHER PUBLICATIONS

"Tip Location of Peripherally Inserted Central Catheters," JVAD, Summer, 1998, pp. 1-4.
(Continued)

*Primary Examiner* — Bhisma Mehta
*Assistant Examiner* — Bradley Osinski
(74) *Attorney, Agent, or Firm* — Brinks Gilson & Lione (57) ABSTRACT

A system and method for vessel catheterization is provided, having an introducer sheath and a catheter. The introducer sheath can include a handle and a sheath body extending from the handle. An access lumen is provided in the introducer sheath, and can include a tapered portion that is sized to receive a tapered outer surface of the catheter. The catheter may be a central venous catheter, such as a peripherally inserted central catheter, including a hub, a catheter body with at least one lumen extending distally from the hub, and at least one tube extending proximally from the hub. The introducer sheath is preferably a splittable sheath. The catheter can be inserted into the access lumen, and translated until confronting surfaces of the tapered outer surface of the catheter body and the tapered portion of the introducer sheath contact one another. This arrangement can inhibit buckling and/or kinking of the catheter during insertion, and improve initial catheter tip positioning.

19 Claims, 10 Drawing Sheets

(56) References Cited

U.S. PATENT DOCUMENTS

| | | | |
|---|---|---|---|
| 4,650,472 | A | 3/1987 | Bates |
| 4,738,658 | A | 4/1988 | Magro et al. |
| 4,840,622 | A | 6/1989 | Hardy |
| 4,921,485 | A * | 5/1990 | Griffiths ............... 604/104 |
| 5,380,304 | A | 1/1995 | Parker |
| 5,454,790 | A | 10/1995 | Dubrul |
| 5,807,398 | A | 9/1998 | Shaknovich |
| 5,830,196 | A | 11/1998 | Hicks |
| 5,849,269 | A | 12/1998 | Burgess et al. |
| 5,895,378 | A | 4/1999 | Nita |
| 6,080,141 | A * | 6/2000 | Castro et al. ............ 604/523 |
| 6,146,381 | A | 11/2000 | Bowe et al. |
| 6,240,231 | B1 | 5/2001 | Ferrera et al. |
| 6,602,241 | B2 | 8/2003 | Makower et al. |
| 6,824,553 | B1 | 11/2004 | Samson et al. |
| 6,884,233 | B2 | 4/2005 | Dance et al. |
| 6,939,337 | B2 | 9/2005 | Parker et al. |
| 7,076,285 | B2 | 7/2006 | Windheuser et al. |
| 7,534,250 | B2 | 5/2009 | Schaeffer et al. |
| 7,637,893 | B2 | 12/2009 | Christensen et al. |
| 2004/0030319 | A1 * | 2/2004 | Korkor et al. ............ 604/506 |
| 2004/0073163 | A1 | 4/2004 | Tomaschko et al. |
| 2005/0080398 | A1 | 4/2005 | Markel et al. |
| 2005/0256503 | A1 | 11/2005 | Hall |
| 2006/0083772 | A1 * | 4/2006 | DeWitt et al. ............ 424/426 |
| 2006/0135973 | A1 | 6/2006 | Hawkins et al. |
| 2007/0185383 | A1 | 8/2007 | Mulhern et al. |
| 2008/0045928 | A1 | 2/2008 | Simpson et al. |
| 2008/0243165 | A1 | 10/2008 | Mauch et al. |
| 2009/0018525 | A1 | 1/2009 | Waite et al. |
| 2009/0105651 | A1 | 4/2009 | Wada et al. |
| 2009/0105652 | A1 | 4/2009 | Beal et al. |

FOREIGN PATENT DOCUMENTS

| | | |
|---|---|---|
| EP | 1 084 728 A1 | 3/2001 |
| WO | WO 2005/004967 A2 | 1/2005 |
| WO | WO 2006/063020 A1 | 6/2006 |

OTHER PUBLICATIONS

Capers, Jo, et al., "Catheter Tip Position as a Risk Factor for Thrombosis Associated with the Use of Subcutaneous Infusion Ports," Support Care Cancer, 2005, vol. 13, pp. 325-331.

Schutz, Jakob C.L., et al., "Relationship Between Chest Port Catheter Tip Position and Port Malfunction After Interventional Radiologic Placement," JVIR, vol. 15, No. 6, Jun. 2004, pp. 581-587.

* cited by examiner

FIG. 5D

METHOD OF INTRODUCING A CATHETER

TECHNICAL FIELD

This application claims the benefit under 35 U.S.C. §121 as a division of U.S. patent application Ser. No. 12/849,501, filed Aug. 3, 2010, which is hereby incorporated by reference herein.

BACKGROUND

Central venous system access in a patient is an important aspect of administering intravenous therapy, such as drug, chemotherapy, and total parenteral nutrition (TPN). It is desirable that the therapy be administered in the superior vena cava (SVC) of the central venous system. In order to gain access, introducer devices are commonly used, through which other medical devices, such as central venous catheters (CVC), are inserted. One such example of a CVC is a peripherally inserted central catheter (PICC). A PICC typically has one or more tubes, which are externally accessible by a clinician, that converge into a single catheter body that is internally implanted in a vein of the patient. The tubes are adapted to receive therapeutic agents, which are then released through a distal tip of the catheter body into the central venous system of the patient.

The most common technique used by the clinician to gain access to the central venous system of the patient with a PICC is a modified Seldinger technique. This technique involves the clinician first inserting a needle through the patient's skin at a peripheral location and into a vein to form a venotomy. The clinician then inserts the guidewire through the passageway of the needle and into the vein. The distal end of the guidewire may then be translated to the target site. Next, the clinician removes the needle from the proximal end of the guidewire, and following removal of the needle the clinician inserts an introducer device and dilator assembly over the proximal end of the guidewire and into the vein. The introducer device and dilator assembly typically includes a splittable introducer device and a dilator to facilitate the ease of insertion and creation of a larger opening in the venotomy. The clinician then removes the dilator, and may even subsequently remove the guidewire from the lumen of the introducer device, leaving the introducer device inserted in the body. The clinician usually with the use of the guidewire determines a suitable length of the PICC and then trims the PICC accordingly.

Figure 1:
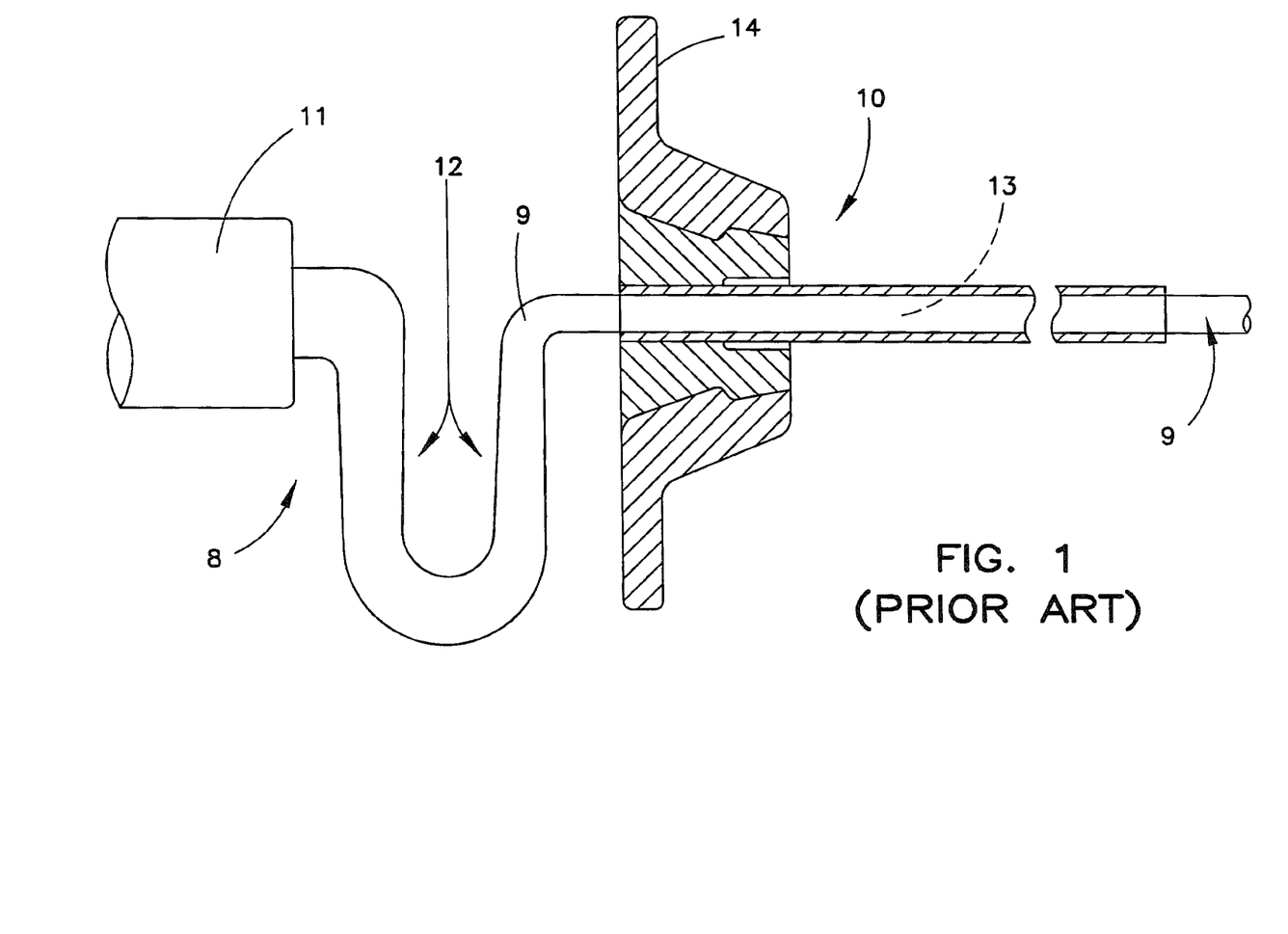
FIG. 1 is a side elevation view of a prior art system for vessel catheterization, depicting a catheter introduced within an introducer device, with a portion of the catheter dangling external to the introducer device.

Next, with reference to FIG. 1, a PICC 8 is inserted through introducer device 10 in order to gain access to the vein and eventually the SVC of the central venous system. PICC 8 has a catheter body 9 extending from a manifold 11, with a portion 12 of catheter body 9 adjacent manifold 11 shown to be tapered. PICC 8 is shown inserted through a constant diameter passageway 13 of introducer device 10. As can be seen, the constant diameter passageway 13 is only sized to receive most of catheter body 9 of PICC 8, essentially until the size of the catheter body at tapered portion 12 is greater than the size of passageway 13. As a result, tapered portion 12 is left dangling external to a handle 14 of introducer device 10. This arrangement is problematic because the dangling tapered portion 12 (about 10-15 cm) can result in an increase in patient discomfort at the access site.

Furthermore, the distal tip of PICC 8 is initially positioned short of its preferred target site by about the same amount as the length of the dangling tapered portion 12. The preferred target site to position a distal tip of a PICC is the lower one-third of the SVC, close to the junction of the SVC and the right atrium. At this location, it has been found that complications from thrombosis and infection are considerably reduced. One factor for this reduction is the ability of the distal tip of the PICC to float freely within the vein lumen at this location and to lie parallel to the vein wall without impinging on the wall. Any impinging of the vein wall from the PICC is known to cause irritation, if not damage, to the vein wall.

Since the distal tip of PICC 8 is not initially positioned at its preferred target site, the clinician must then perform a series of alternating steps of peeling a small part of introducer device 10 away from the implanted PICC 8 and translating the distal tip of PICC 8 closer to the target site until the distal tip of the PICC is at the preferred target site. However, when performing the series of alternating steps, the clinician must manipulate tapered portion 12 of catheter body 9 of PICC 8, leaving the catheter body along this portion highly susceptible to buckling and kinking. Not until the clinician is satisfied with the location of the distal tip of the PICC does this risk of buckling reduce. Buckling and kinking of PICC 8 is highly undesirable because the PICC becomes essentially useless for its intended purpose. At that point, a new PICC must be inconveniently reinserted into the vein by starting over at the very beginning with the modified Seldinger technique, which can extend the procedure time and further delay the administration of intravenous therapy.

Thus, what is needed is an introducer device that is configured to receive a catheter to permit the distal tip of the catheter to reach a target site, e.g., the central venous system, during its initial insertion through the introducer device. Further, what is needed is an introducer device that is configured to receive a catheter to limit, if not eliminate, any external dangling portion of the catheter and its associated risks to buckling and/or kinking during insertion through the introducer device. What is also needed is a catheterization system, and method of use thereof for therapeutic treatment, such as therapeutic treatment of the central venous system, that can cause less discomfort and inconvenience to the patient.

BRIEF SUMMARY

In a first embodiment, an introducer sheath for vessel catheterization is provided. The sheath can include a sheath body and a handle. The sheath body has a proximal end and a distal end, and a passageway extending longitudinally therethrough. The handle can be attached to the proximal end of the sheath body. The handle can include an opening extending from a proximal end to a distal end. The opening can be in communication with the passageway of the sheath body, which together define an access lumen of the introducer sheath. A first tab and a second tab may be disposed on opposite sides of the opening. A weakened region can be oriented in the longitudinal direction so that the handle is capable of being split when the first and second tabs are pulled apart from one another. The access lumen can have a tapered portion that is sized to receive a tapered outer surface of a catheter. Preferably, the tapered portion has a continuously smooth taper. The body of the introducer sheath disposed about the tapered portion of the access lumen can also be tapered, preferably at the same tapering rate as the tapered outer surface of the catheter. An introducer sheath having a tapered body to define a tapered portion of the access lumen can more quickly provide hemostasis at the puncture site, can provide enhanced strain relief along the introducer sheath body, and/or can be easier to split along the weakened portion of the introducer sheath due to mechanical advantage from the tapered body.

In a second embodiment, a system for vessel catheterization is also provided. The system can include an embodiment of a catheter assembly in addition to one of the embodiments of an introducer sheath, as described herein. The catheter assembly is preferably a central venous catheter, such as a peripherally inserted central catheter, for insertion and access to a central venous system of a patient. The catheter assembly can include a catheter body, a hub assembly, and at least one tube. The catheter body can have a tapered outer surface along a length thereof. The catheter body can have one or more lumens extending longitudinally therethrough, with the body extending distally from the hub assembly. The tube can have a lumen extending longitudinally therethrough, with each tube extending proximally from the hub assembly. The hub assembly can have a body adapted to provide a fluid transition from the lumen of the tube(s) to the lumen(s) of a single catheter body. The catheter body preferably has a tapered outer surface along the length thereof, preferably adjacent the hub assembly. The catheter body may also include an antimicrobial drug coating along a portion of at least one of an outer surface or a luminal surface along at least one of the lumen(s). A system with an introducer sheath having an access lumen with a tapered portion and a catheter with a tapered portion can provide a reduced risk of buckling and kinking of the catheter's tapered portion during insertion and translation of the catheter into the body vessel and/or can facilitate a closer initial tip position relative to the target site.

In a third embodiment, a method of vessel catherization, for example to provide intravenous therapy to a patient, is provided. The method can include one or more of the following steps: creating an entry opening in a body vessel; introducing a distal end of one of the embodiments of the introducer sheath described herein through the entry opening to inside the body vessel; introducing a catheter body of one of the embodiments of a catheter assembly described herein to inside the body vessel, through an access lumen of the introducer sheath; translating the catheter body in the body vessel until confronting surfaces of a tapered outer surface of the catheter body and a tapered portion of the introducer sheath contact one another. This method can significantly reduce the number of steps, and time associated therewith, when gaining percutaneous access to a body vessel for treatment such as to administer intravenous therapy more quickly.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of inventive devices, as well as the axial ends of various component features. The term "proximal" is used in its conventional sense to refer to the end of the device (or component thereof) that is closest to the clinician during use of the device. The term "distal" is used in its conventional sense to refer to the end of the device (or component thereof) that is initially inserted into the patient, or that is closest to the patient during use.

Figure 2:
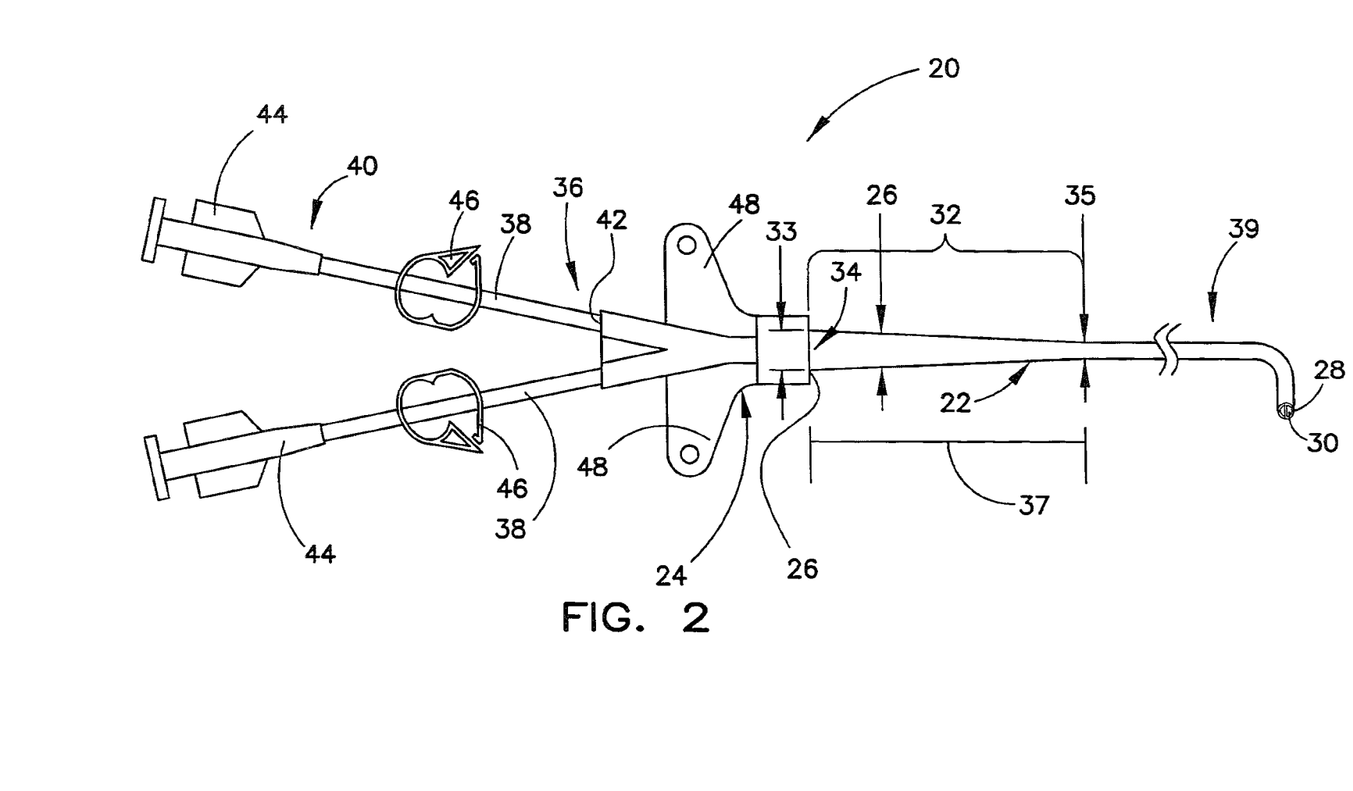
FIG. 2 is a side elevation view of a catheter used in a system for vessel catheterization.

FIG. 2 shows an exemplary central venous catheter (CVC) 20, such as a peripherally inserted central catheter (PICC), for insertion into a body vessel of a patient so that access to a central venous system can be provided. One desirable target site in the central venous system is the superior vena cava (SVC), and preferably, the lower one-third of the SVC, close to the junction of the SVC and the right atrium. At this preferred target site, complications from thrombosis and infection can be minimized.

Catheter 20 includes a catheter body 22 extending distally from a hub assembly 24 and having a length suitable to reach the intended target site. For example, the catheter length can be up to about 50-60 cm, although it can be trimmed to suitable size as necessary. Catheter body 22 has a proximal end 26 and a distal tip 28, and one or more lumens 30 extending through the catheter body. An outer portion 32 corresponding to the proximal end of catheter body 22 tapers down from a first diameter 33 to a second diameter 35 for a predetermined longitudinal distance 37. Longitudinal distance 37 may be a suitable distance to extend through the body just short of the body vessel, and may even extend into the body vessel. It is desirable to make the first and second diameters as small as possible to limit the amount of space during the indwelling of the catheter body within the body. The difference is sizes for first and second diameters 33, 35 can be sized up to about 2-3 French sizes. Longitudinal distance 37 can be any distance necessary but typically in the range of 3-4 cm up to about 10-15 cm.

Tapered outer portion 32 of the catheter body is typically larger than the puncture opening and can be used to provide immediate hemostasis when pushed slightly more into the opening for sealing along the edge of the puncture opening. A remaining portion 39 of catheter body 22, distal to tapered outer portion 32 and extending to distal tip 28, typically has a constant diameter. Remaining portion 39 is generally the same diameter as second diameter 35 at the end of tapered outer portion 32. Catheter body 22 can be made of medical grade polymers, such as polyurethane or silicone. Markings can be placed on the catheter body to indicate incremental distances, e.g., every 1 cm or 5 cm, so that the intended length of the catheter body can be easily determined for trimming.

Hub assembly 24 includes a first port 34 where the proximal end 26 of catheter body 22 attaches thereto, and one or more second ports 36. Extending proximally from each second port 36 is a tubular member 38 having a proximal end 40 and a distal end 42. Hub assembly 24 is a structure that provides a fluid transition from one or more discrete tubular members 38 (e.g., 1, 2, 3, 4, 5 or more tubular members) at one end to typically a corresponding number of separate, noncommunicating lumens 30 (e.g., 1, 2, 3, 4, 5, or more lumens) that are located within a single catheter body 22. For example, FIG. 2 shows a first and a second tubular member 38 at one end of the hub assembly, and a single catheter body 22 having a FIG. 8, dual lumen 30 on the other side. A connector 44, e.g., a luer connector, can be attached to proximal end 40 of each tubular member 38. A clamping device 46 can be disposed around each of tubular members 38 and is capable of shutting off fluid flow through the tubular members and preventing air aspiration due to inadvertent hub dislodgement. Hub assembly 24 may also have one or more attachment wings 48 for facilitating attachment to the body of the patient.

One or more coatings may be associated with catheter body 22. Such coating may comprise a hydrophilic coating, a lubricous coating, and/or a drug coating. The coating can be associated with the catheter body by any suitable manner known in the art, such as dipping, spraying, impregnation, and the like. The drug coating can be an antimicrobial useful in treating catheter-related blood stream infections, such as methicillin-resistant *Staphylococcus aureus* (MRSA), VARS, and vancomycin-resistant *enterococcus* (VRE). One such drug coating that can be beneficial in inhibiting the blood infections can comprise at least one of minocycline and rifampin. One exemplary catheter having a drug combination coating of minocycline and rifampin is the SPECTRUM® Turbo-JeCT™ PICC, which is available at Cook Medical Incorporated in Bloomington, Ind.

Figure 3:
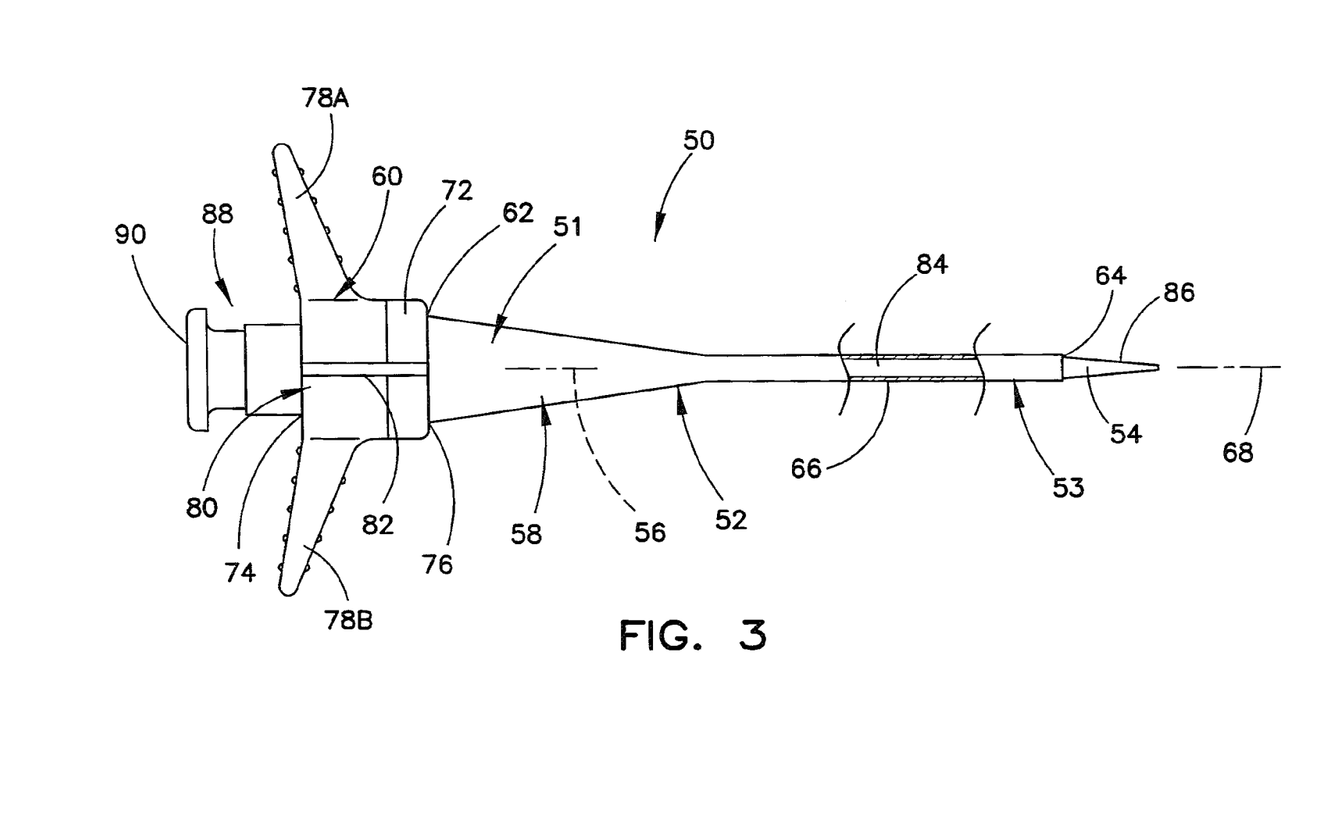
FIG. 3 is a side elevation view of an introducer sheath with a dilator that is used in a system for vessel catheterization.

FIG. 3 shows an exemplary introducer sheath assembly 50 including an introducer sheath 52 and a dilator 54. Introducer sheath assembly 50 can be used over a guidewire, and can be adapted to provide external access to a body vessel. Since catheter 20 typically does not have a tip to puncture the skin and/or is not adapted to access the vessel of its own, introducer sheath assembly 50 can be well suited for providing vessel access for catheter 20, as described in more detail below. Dilator 54 is shown inserted completely through an access lumen 56 of introducer sheath 52 and locked to the introducer sheath. Introducer sheath 52 includes a sheath body 58 extending from a handle 60.

Sheath body 58 is a tubular body having a proximal end 62 and a distal end 64, with a passageway 66 extending longitudinally therethrough about a longitudinal axis 68. Sheath body 58 can be made of low friction biocompatible polymers or fabrics. Non-limiting examples of a suitable material for the sheath body includes polytetrafluoroethylene (PTFE), ePTFE, polyethylene terephthalate (PET), polyamides such as nylon, polyether amide (PEBA), polyurethanes, or the like. To increase lubricity, the sheath body can also be coated with a hydrophilic coating as appreciated in the art.

Figure 3A:
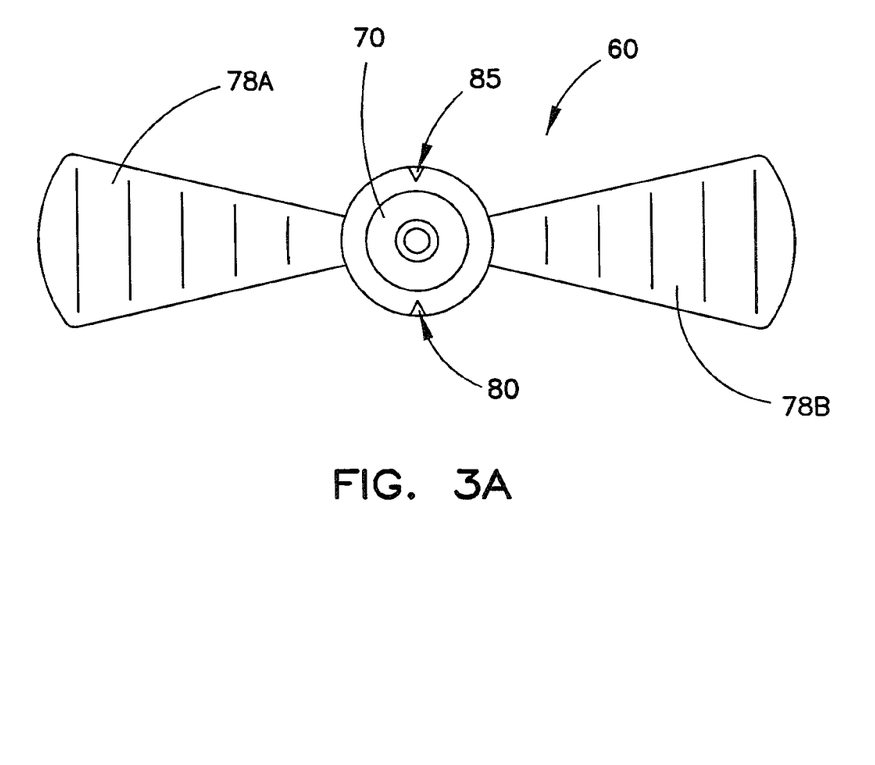
FIG. 3A is an end view of the introducer sheath of FIG. 3, with the dilator removed therefrom.

According to FIGS. 3 and 3A, handle 60 is shown attached to proximal end 62 of sheath body 58. Handle 60 includes an opening 70 extending through a central portion of a handle body 72 along longitudinal axis 68. Handle opening 70 has a proximal end 74 and a distal end 76 and is positioned such that the handle opening is in fluid communication with passageway 66 of sheath body 58 to define together the entire access lumen 56 of introducer sheath 52.

Handle 60 can further include one or more tabs. A first tab 78A and a second tab 78B are shown disposed on opposite sides, preferably diametrically opposite, of handle opening 70, and extending radially outward away from longitudinal axis 68. Tabs 78A, 78B provide support for the fingers and/or thumb of the clinician and enhanced control and handling of the device during its use. Handle 60 can be formed from any rigid or semi-rigid material having sufficient structural strength for the purposes described herein. Preferably, handle 60 is insert-molded over the proximal end of the sheath body.

Handle 60 preferably has a weakened region 80 in a longitudinal direction, so that introducer sheath 52 is capable of being longitudinally split for removal from the patient's body. Weakened region 80 may facilitate the splitting of at least a portion of sheath body 58 as well. In other words, when tabs 78A, 78B are pulled radially apart from one another and downward, handle 60 and at least a portion of sheath body 58 can be readily removed by peeling introducer sheath 52 away from a device that is inserted in its access lumen. Weakened region 80 can include a pair of axial slots 82, as shown in FIGS. 3 and 3A, to create a region of relatively thin material. The weakened region may further include a longitudinal region of softer material, a series of perforations, or other structural features to facilitate removing of the introducer sheath as known in the art. The tabs can be a variety of shapes and can even include surface irregularities to improve its gripping when being manipulated and pulled apart.

Figure 4:
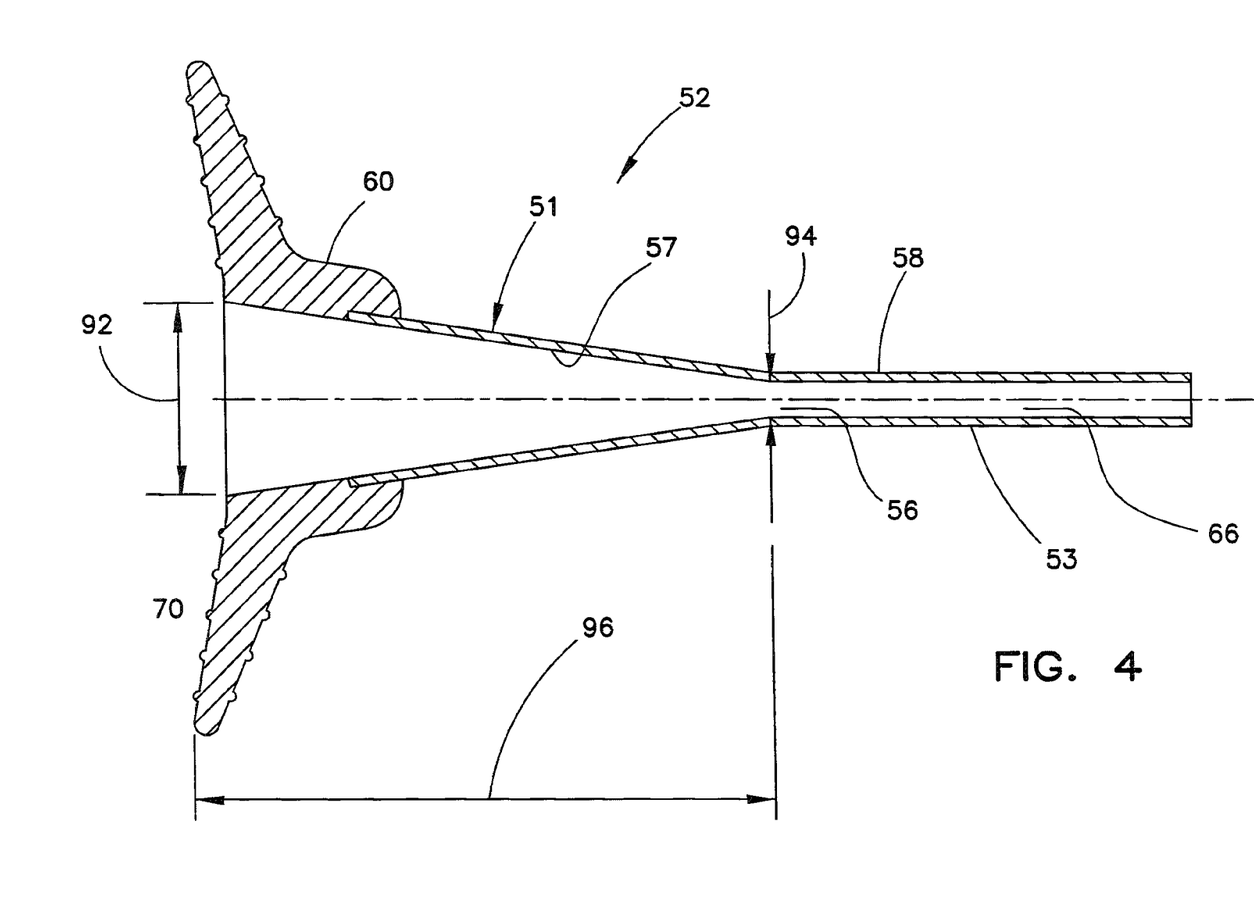
FIG. 4 is a cross-sectional view of the introducer sheath of FIG. 3, with the dilator removed therefrom.

Access lumen 56 is adapted to allow the passage of other medical devices, such as the aforementioned dilator 54 and catheter 20. As shown in FIG. 4, introducer sheath assembly 50 can include a tapered outer portion 51 along its outside surface and a distal portion 53 with a constant diameter, although the entire length of the body can be tapered. The tapered outer portion 51 can provide hemostasis at the puncture site more quickly by increasing the distance of insertion of introducer sheath 52 into the vessel opening to create a tighter seal. Tapered outer portion 51 may also provide enhanced strain relief along sheath body 58, and a smoother transition from handle 60 to sheath body 58, to avoid potential stress risers and kinking. Further, tapered outer portion 51 provides material farther away from the axis 68 than conventional introducer sheaths, and at an angle to axis 68, to provide a mechanical advantage for initially breaking handle 60 along weakened portion 80 and for splitting the handle and the sheath body.

Referring back to FIG. 3, dilator 54 has a longitudinal body, with a substantial portion 84 thereof having a diameter approximately equal to the diameter of access lumen 56 along distal portion 53 of introducer sheath 52. Dilator 54 may also have portion that is tapered in a similar manner as a tapered inner portion of the access lumen described below in order to improve the internal fit and inhibit the dilator from being inserted too far into the access lumen. Dilator 54 also has a distal end 86 shown extending beyond distal end 64 of sheath body 58. Distal end 86 can be tapered to an even smaller diameter in order to facilitate insertion of introducer sheath 52 into the body vessel. Dilator 54 may also have a connector 88, e.g., a threaded luer connector, which is capable of being attached to handle 60 of the introducer sheath. In one example, dilator connector 88 can be adapted to removably attach with handle 60, e.g., handle opening 70, for easy removal from introducer sheath 52. In addition, dilator 54 may also include a connector 90, e.g., a luer connector, at its proximal end for attachment to devices used for flushing the system, and may include an injection cap (not shown) that is placed over the proximal end of dilator 54.

FIG. 4 further depicts access lumen 56 of introducer sheath 52 including a tapered inner portion 57 that has been exaggerated for clarity. Tapered inner portion 57 tapers from a first diameter 92 to a second diameter 94. First diameter 92 can be located at some point along handle opening 70 and/or near the proximal end of sheath body 58. Second diameter 94 can be located along a portion of passageway 66 of sheath body 58 at a pre-determined longitudinal distance 96 from first diameter 92. Tapered inner portion 57 preferably is sized to be at least approximately the size of tapered outer portion 32 of catheter 20. In other words, first diameter 92 of access lumen 56 is sized to be at least as large as first diameter 33 of catheter body 22. Further, second diameter 94 of access lumen 56 is sized to be at least as large as second diameter 35 of catheter body 22. To minimize the amount of space in the body during indwelling the introducer sheath, first diameter 92 of access lumen 56 can be sized to match first diameter 33 of catheter body 22 and second diameter 94 of access lumen 56 can be sized to match second diameter 35 of catheter body 22. However, to more easily facilitate the receiving of the catheter body, first diameter 92 of access lumen 56 may be sized 0.5 to 1 French greater than first diameter 33 of catheter body 22 and second diameter 94 of access lumen 56 may be sized 0.5 to 1 French greater than second diameter 35 of catheter body 22. Further, along the distal portion 53 of the introducer sheath assembly 50, access lumen 56 preferably is of a constant diameter sized to be at least as large as distal portion 39 of the catheter, although the entire length of the lumen can be tapered. The tapered portion of the access lumen can be tapered at approximately the same rate as the tapered outer surface of the catheter, e.g., a tapering rate in the range of 1/1.5 French size/cm to about 1/7.5 French size/cm.

Figure 4A:
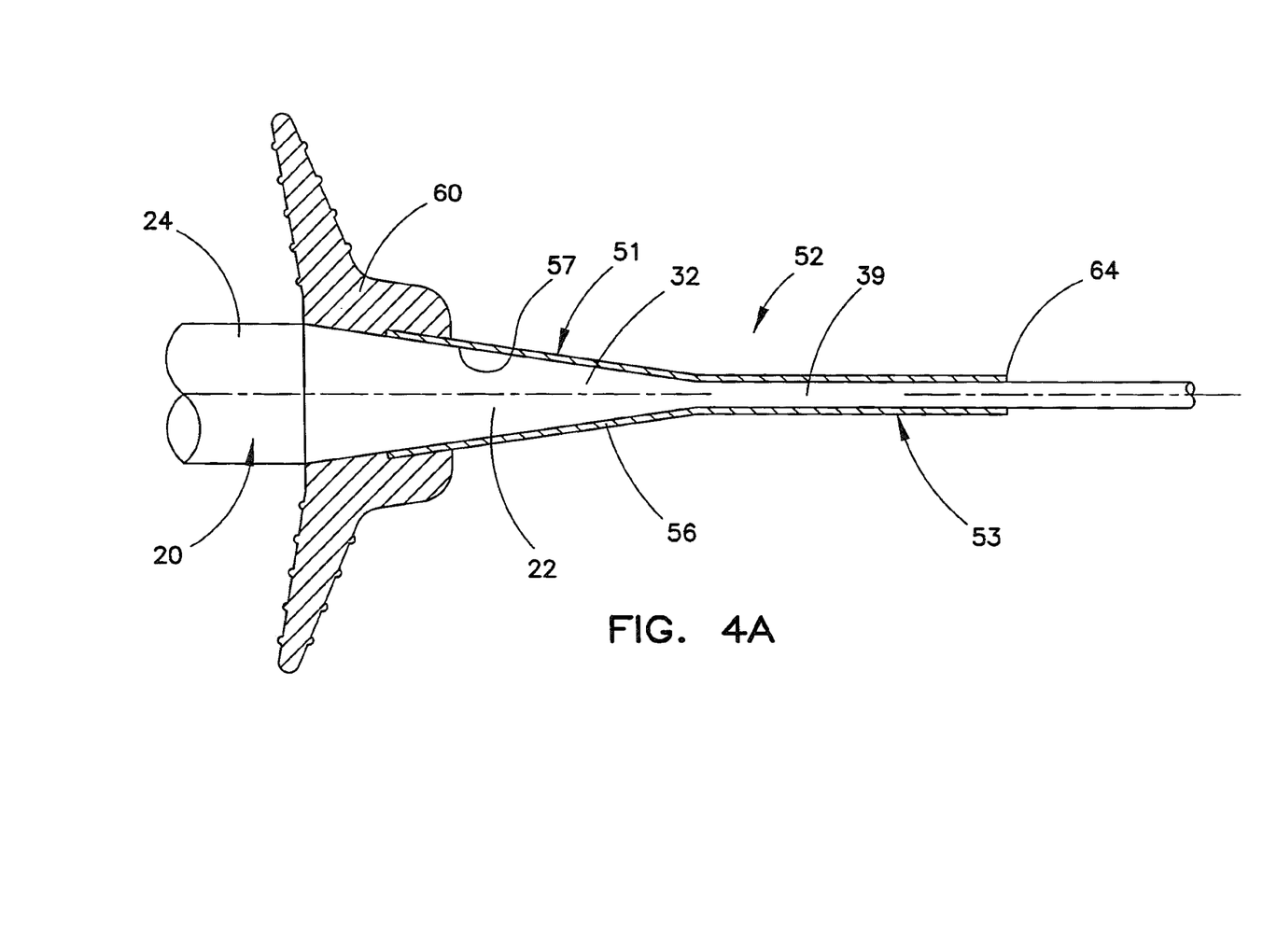
FIG. 4A is a cross-sectional view of the introducer sheath of FIG. 3, with the catheter of FIG. 2 introduced in the place of the dilator, depicting a system for vessel catheterization.

As depicted in FIG. 4A, when inserted into access lumen 56 of introducer sheath 50, catheter body 22 of catheter 20 is translated in the body vessel until tapered outer surface 32 of the catheter body confronts tapered inner portion 57 of access lumen 56. This arrangement may even be sized to permit hub assembly 24, to contact handle 60 to indicate to the clinician that distal tip 28 of catheter 20 is positioned at its preferred target site. To this end, tapered inner portion 57 of access lumen 56 receives substantially the entire tapered outer surface 32 of catheter 20 up to hub assembly 24 to reduce the risks associated with portions of the catheter dangling external to the access site. This arrangement can provide a reduced risk of buckling and/or kinking of the catheter external to the introducer sheath during initial translation of the catheter. Further, the luminal walls that define access lumen 56 can provide a guiding surface to further inhibit buckling and/or kinking of the catheter disposed internally within the introducer sheath during the final translation of the last portion of the catheter to the target site. This arrangement can also permit distal tip 28 of catheter 20 to be positioned initially closer to (e.g., up to about 10-15 cm), if not at, the target site when compared to conventional devices as shown in FIG. 1.

With reference now to FIGS. 5A-5D, a method of vessel catherization will now be described with specific reference to intravenous therapy using the central venous system of a patient with introducer sheath 52 and catheter 20. One skilled in the art can appreciate that the method described herein can be used for other treatments and therapies for other types of body vessels and lumens, other than intravenous therapy.

Figure 5A:
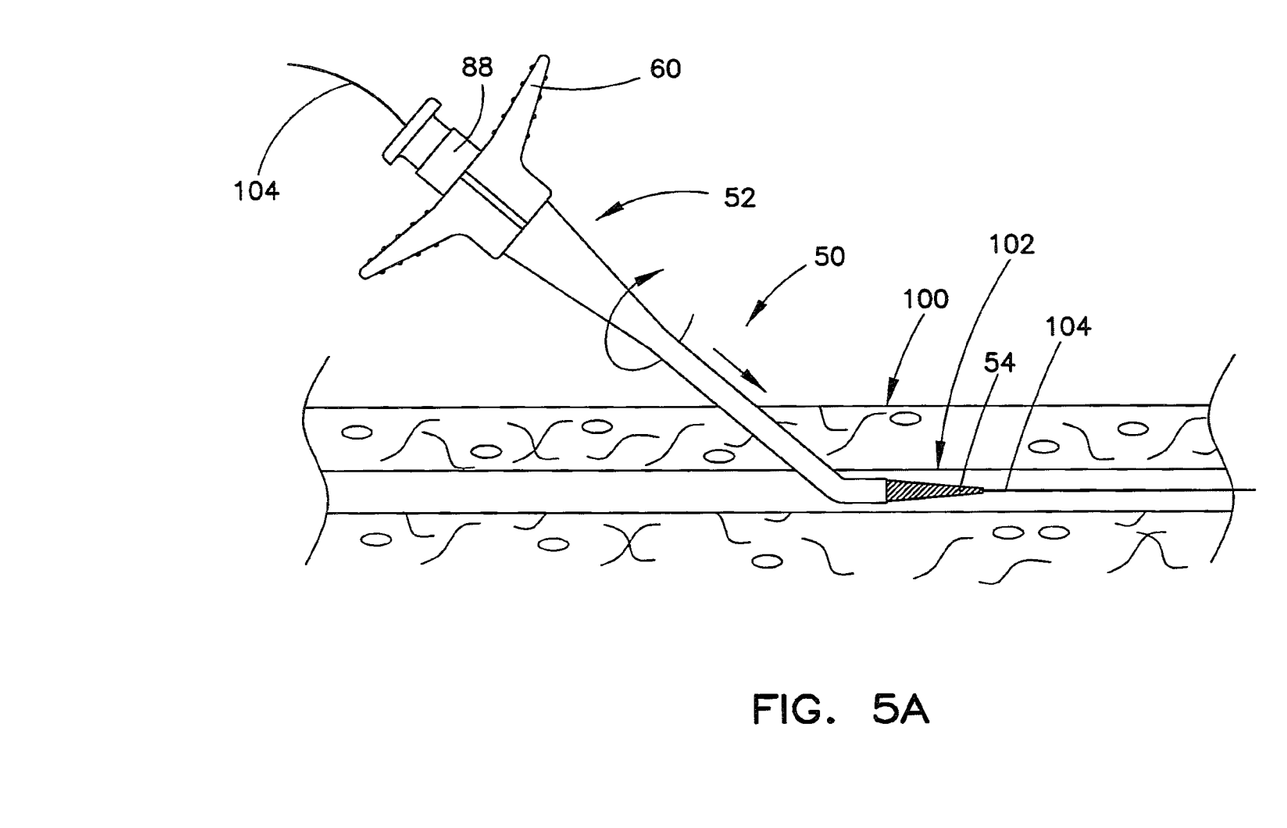
FIGS. 5A-5D are side elevation views, depicting various steps of a method of using a system for vessel catheterization of a body vessel of a patient.

A clinician can gain central venous system access by using a standard or modified Seldinger technique. After prepping the access site, an access needle (not shown) is inserted through skin 100 of a patient to create an opening or venotomy in a body vessel, such as a vein 102, where external access to inside of vein 102 is gained. For intravenous therapy, one of the basilic vein, cephalic vein or brachial vein is typically used. The use of ultrasound may be helpful to determine the suitability for venous access and patency. A guidewire 104 is inserted through the access needle and is translated a distance, e.g., 15-20 cm into vein 102, generally using fluoroscopic guidance. The access needle is then removed, leaving guidewire 104 in place.

According to FIG. 5A, introducer sheath assembly 50 with introducer sheath 52 and dilator 54 is then inserted over guidewire 104 and into vein 102. Introducer sheath assembly 50 may need to be twisted in order to be advanced farther into vein 102 in order to implant a substantial portion of sheath body 50 within the subcutaneous portion of skin 100. When the initial guidewire is not long enough to access the desired target site, it can removed, and another longer and/or stronger guidewire can be introduced through introducer sheath assembly 50 into vein 102 and translated to the desired target site. The longer guidewire, also referred to as reference numeral 104, is typically marked at 1 cm or 5 cm increments to indicate the distance from the access site to the target site. Catheter 20 can then be trimmed to suitable size according to the measured distance. Leaving introducer sheath 52 and the guidewire 104 in place, dilator 54 can then be removed from introducer sheath 52 by unlocking connector 88 from handle 60 of introducer sheath 52. It can be appreciated by those skilled in the art that the longer guidewire 104 can also be removed, leaving only the introducer sheath in place.

Figure 5B:
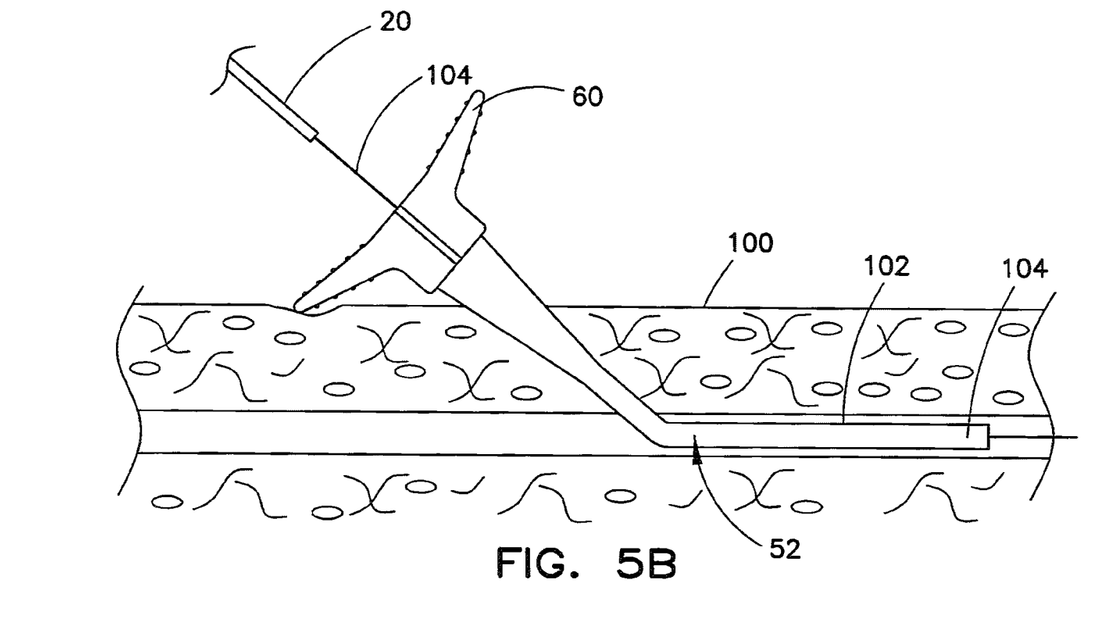
Figure 5C:
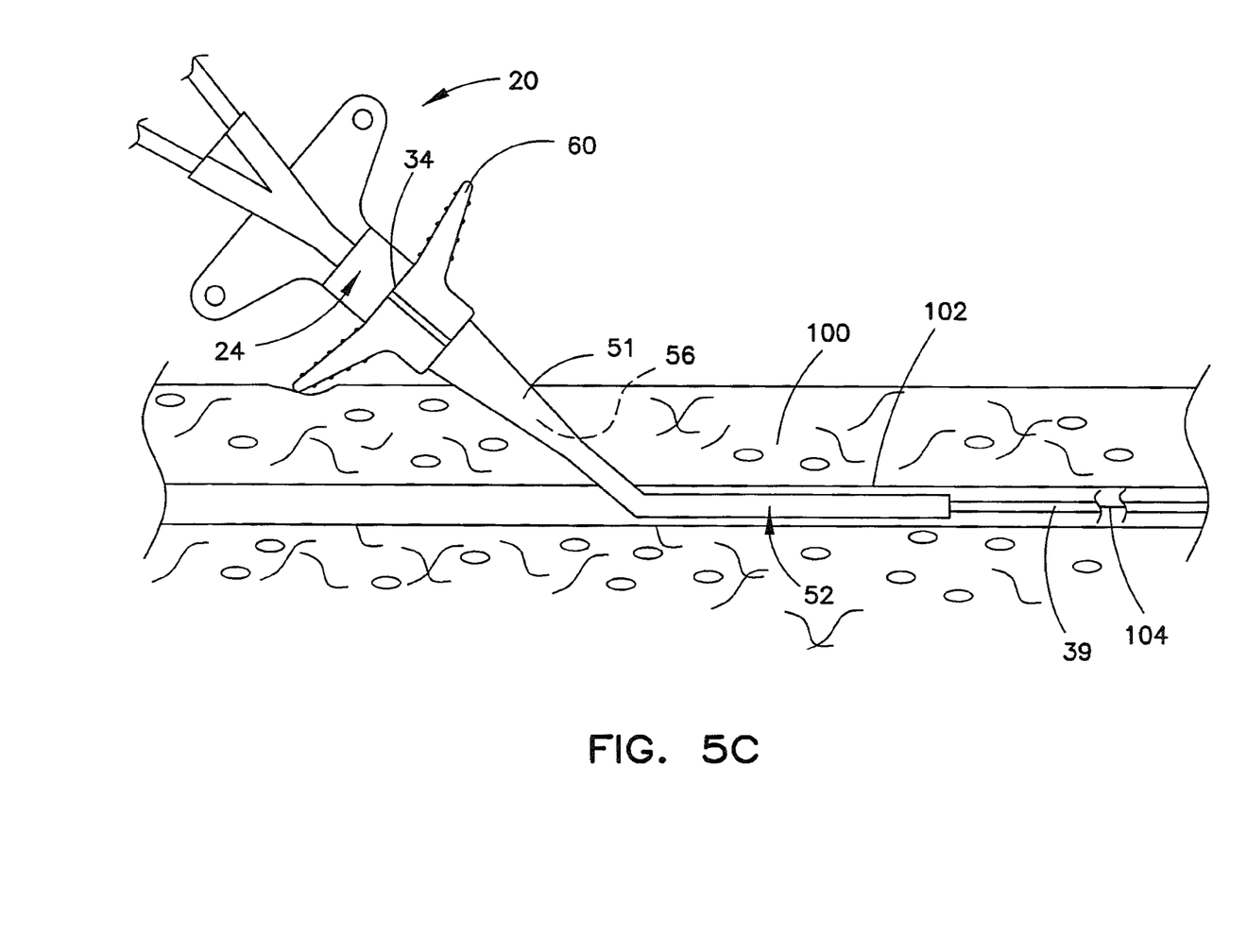

According to FIG. 5B, catheter 20 is then inserted over guidewire 104, through introducer sheath 52, and then translated over guidewire 104 within vein 102 to the target site. Again, the catheter can be inserted through the introducer sheath and translated to the target site after removal of the guidewire. According to FIG. 5C, catheter 20 is inserted into access lumen 56 of introducer sheath 52. Catheter 20 is translated distally until confronting surfaces of the tapered outer surface of catheter body 22 and the tapered inner portion of access lumen 56 contact one another, and preferably until distal end 34 of catheter hub assembly 24 contacts handle 60 of introducer sheath 52 (as shown in FIG. 4A). Distal portion 39 of catheter 20 is shown extending distally past the end of introducer sheath 52. Tapered portion 32 of catheter 20 can be advantageously inserted entirely into the access lumen 56 of introducer sheath 52. Further, while introducer sheath 52 is in place, the distal tip of catheter 20 is preferably translated to the target site.

Figure 5D:
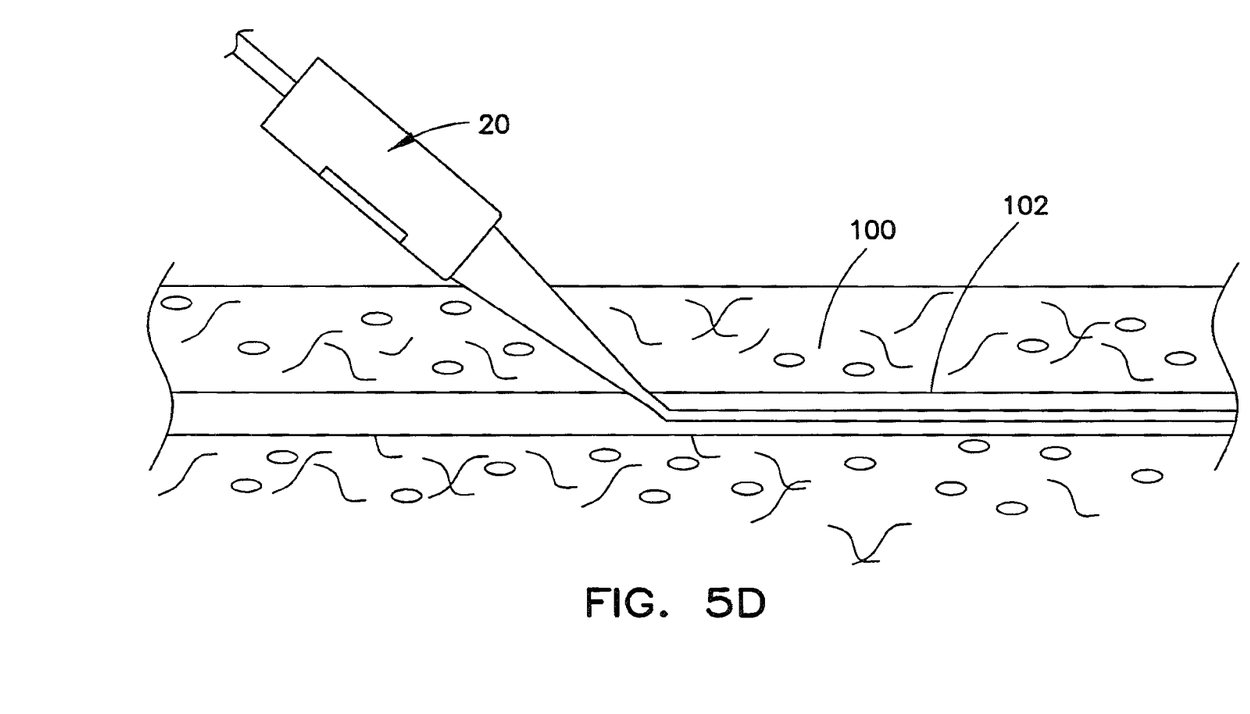

Before removal of introducer sheath 52, the location of the catheter distal tip can be radiographically verified with imaging equipment to ensure the distal tip is at its intended location. To remove introducer sheath 52 that is implanted within the subcutaneous portion of the skin, the tabs of handle 60 are pulled radially apart from one another and downward to snap or break the handle along the weakened region. Stabilizing catheter 20 in place, introducer sheath 52 while in the subcutaneous portion can then be split apart by continuously pulling the tabs radially apart until the introducer sheath is entirely removed from the catheter. This can be generally performed without affecting the position of catheter 20 within vein 102, as shown in FIG. 5D. Preferably, the clinician can remove the introducer sheath from the catheter by avoiding the series of alternating steps of peeling a small part of introducer sheath away from the catheter and translating the distal tip of the catheter closer to the target site. The tip position of the catheter may again be verified. Even when a small portion (e.g., 0.5-1 cm) of the catheter is translated proximally, the clinician can translate the tapered outer portion of the catheter farther in the venotomy for inhibiting blood loss.

As can be appreciated by those skilled in the art, a source of therapeutic, nutritional, and/or imageable agents, such as syringe or an intravenous (IV) bag, can then be coupled to the connectors of the one or more tubes of catheter 20 (FIG. 2). The therapeutic agent is pressurized in a manner to travel through the tubes and lumens of catheter 20 and to be released to the target site. Catheter 20 can provide short-term or long-term vessel pressure monitoring, blood sampling, administration of drugs and fluids, such as total parenteral nutrition (TPN), chemotherapeutic agents or other therapeutic drugs, and delivery of contrast in computed tomography (CT) studies with power injectors as known in the art.

In one example, a catheter includes a tapered outer surface that tapers from a first diameter of 7 French that is adjacent the hub assembly to a second diameter of 5 French for a longitudinal distance of about 10 cm. An introducer sheath includes an access lumen having a tapered portion that is tapered from a first diameter of 8 French at the proximal end of the handle opening to a second diameter of 5.5 French for a longitudinal distance of about 10 cm from the proximal end of the handle opening. Other introducer sheaths may be proportionally sized in a similar fashion with respect to the different sizes of catheters.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention

We claim:

1. A method of vessel catherization comprising:
   providing a catheter assembly comprising a catheter body and a hub assembly, said catheter body having one or more lumens extending longitudinally therethrough and extending distally from said hub assembly, said catheter body comprising a tapered outer surface adjacent said hub assembly;
   providing an introducer sheath comprising a handle and a sheath body extending from said handle, said introducer sheath having an access lumen extending through said sheath body and said handle, wherein said access lumen has a tapered portion sized to receive said tapered outer surface of said catheter body;
   creating an entry opening through a vessel with a needle;
   introducing said introducer sheath through said vessel entry opening to access said vessel;
   introducing said catheter body of said catheter assembly into said vessel through said access lumen of said introducer sheath; and
   translating said catheter body through said vessel until confronting surfaces of said tapered outer surface of said catheter body and said tapered portion of said introducer sheath contact one another;
   wherein an external dangling portion of said catheter body between said handle of said introducer sheath and said hub assembly of said catheter assembly is limited to inhibit buckling and kinking of said catheter body outside said introducer sheath when said confronting surfaces of said tapered outer surface of said catheter body and said tapered portion of said introducer sheath contact one another.

2. The method of claim 1, further comprising introducing a guidewire into said vessel through said needle, removing said needle after said guidewire is introduced, and introducing said introducer sheath over said guidewire.

3. The method of claim 1, further comprising inserting a dilator through said access lumen of said introducer sheath, said dilator comprising a tapered distal end extending beyond a distal end of said introducer sheath, introducing said introducer sheath with said dilator through said vessel entry opening to access said vessel, and removing said dilator from said access lumen of said introducer sheath before introducing said catheter body through said introducer sheath.

4. The method of claim 1, further comprising trimming said catheter body to a suitable length before introducing said catheter body through said introducer sheath.

5. The method of claim 1, wherein said handle comprises first and second tabs disposed on opposite sides and a weakened region, and further comprising pulling said first and second tabs apart from one another to split said handle along at least said weakened region in order to remove said introducer sheath from said catheter assembly.

6. The method of claim 1, wherein said vessel is part of a venous system, and further comprising introducing at least one of a therapeutic agent, a nutritional agent, and an imageable agent through said catheter assembly.

7. The method of claim 1, wherein said catheter assembly is a peripherally inserted central catheter, and further comprising introducing a therapeutic agent or a nutritional agent through said peripherally inserted central catheter.

8. The method of claim 1, further comprising introducing a therapeutic agent through said catheter assembly, and pressurizing said therapeutic agent.

9. The method of claim 1, wherein a distal end of said catheter assembly is located in a central venous system when said confronting surfaces of said tapered outer surface of said catheter body and said tapered portion of said introducer sheath contact one another.

10. The method of claim 1, wherein a distal end of said catheter assembly is located in a lower one-third of a superior vena cava close to a junction of said superior vena cava and a right atrium when said confronting surfaces of said tapered outer surface of said catheter body and said tapered portion of said introducer sheath contact one another.

11. The method of claim 1, wherein a distal end of said catheter assembly is located within about 15 cm of an intended target site when said confronting surfaces of said tapered outer surface of said catheter body and said tapered portion of said introducer sheath contact one another.

12. The method of claim 1, wherein said hub assembly of said catheter assembly and said handle of said introducer sheath contact each other when said confronting surfaces of said tapered outer surface of said catheter body and said tapered portion of said introducer sheath contact one another, said tapered portion of said introducer sheath receiving an entire length of said tapered outer surface of said catheter body.

13. The method of claim 1, wherein said catheter body is capable of buckling and kinking.

14. The method of claim 1, wherein said catheter body comprises markings to indicate distances for trimming an intended length of said catheter body.

15. The method of claim 1, wherein said catheter assembly comprises at least one tube, said at least one tube having a lumen extending longitudinally therethrough and extending proximally from said hub assembly, said hub assembly comprising a body configured to provide a fluid transition from said lumen of said at least one tube to said one or more lumens of said catheter body.

16. The method of claim 1, wherein said tapered outer surface of said catheter body has a longitudinal length between about 3 cm and about 15 cm, and a difference in an outer diameter of said tapered outer surface is between about 2 French and about 3 French.

17. The method of claim 1, wherein a portion of at least one of an outer surface and a luminal surface of said catheter body comprises an antimicrobial drug coating.

18. A method of vessel catherization comprising:
providing a catheter assembly comprising a catheter body and a hub assembly, said catheter body having one or more lumens extending longitudinally therethrough and extending distally from said hub assembly, said catheter body comprising a tapered outer surface adjacent said hub assembly;
providing an introducer sheath comprising a handle and a sheath body extending from said handle, said introducer sheath having an access lumen extending through said sheath body and said handle, wherein said access lumen has a tapered portion sized to receive said tapered outer surface of said catheter body;
creating an entry opening through a vessel with a needle;
introducing said introducer sheath through said vessel entry opening to access said vessel;
trimming said catheter body to a suitable length before introducing said catheter body through said introducer sheath;
introducing said catheter body of said catheter assembly into said vessel through said access lumen of said introducer sheath; and
translating said catheter body through said vessel until confronting surfaces of said tapered outer surface of said catheter body and said tapered portion of said introducer sheath contact one another;
wherein said handle comprises first and second tabs disposed on opposite sides and a weakened region, and further comprising pulling said first and second tabs apart from one another to split said handle along at least said weakened region in order to remove said introducer sheath from said catheter assembly,
wherein said vessel is part of a venous system, and further comprising introducing at least one of a therapeutic agent, a nutritional agent, and an imageable agent through said catheter assembly, and
wherein a distal end of said catheter assembly is located in a central venous system when said confronting surfaces of said tapered outer surface of said catheter body and said tapered portion of said introducer sheath contact one another, an external dangling portion of said catheter body between said handle of said introducer sheath and said hub assembly of said catheter assembly is limited to inhibit buckling and kinking of said catheter body outside said introducer sheath when said confronting surfaces of said tapered outer surface of said catheter body and said tapered portion of said introducer sheath contact one another, and said catheter body is capable of buckling and kinking.

19. The method of claim 18, further comprising introducing a guidewire into said vessel through said needle, removing said needle after said guidewire is introduced, and introducing said introducer sheath over said guidewire, inserting a dilator through said access lumen of said introducer sheath, said dilator comprising a tapered distal end extending beyond a distal end of said introducer sheath, introducing said introducer sheath with said dilator through said vessel entry opening to access said vessel, and removing said dilator from said access lumen of said introducer sheath before introducing said catheter body through said introducer sheath, wherein said catheter assembly is a peripherally inserted central catheter, and further comprising introducing a therapeutic agent through said peripherally inserted central catheter, and pressurizing said therapeutic agent, wherein said distal end of said catheter assembly is located in a lower one-third of a superior vena cava close to a junction of said superior vena cava and a right atrium when said confronting surfaces of said tapered outer surface of said catheter body and said tapered portion of said introducer sheath contact one another, said distal end of said catheter assembly is located within about 15 cm of an intended target site when said confronting surfaces of said tapered outer surface of said catheter body and said tapered portion of said introducer sheath contact one another, said hub assembly of said catheter assembly and said handle of said introducer sheath contact each other when said confronting surfaces of said tapered outer surface of said catheter body and said tapered portion of said introducer sheath contact one another, said tapered portion of said introducer sheath receiving an entire length of said tapered outer surface of said catheter body, said catheter body comprises markings to indicate distances for trimming an intended length of said catheter body, said catheter assembly comprises at least one tube, said at least one tube having a lumen extending longitudinally therethrough and extending proximally from said hub assembly, said hub assembly comprising a body configured to provide a fluid transition from said lumen of said at least one tube to said one or more lumens of said catheter body, said tapered outer surface of said catheter body has a longitudinal length between about 3 cm and about 15 cm, and a difference in an outer diameter of said tapered outer surface is between about 2 French and about 3 French, and a portion of at least one of an outer surface and a luminal surface of said catheter body comprises an antimicrobial drug coating.

* * * * *

UNITED STATES PATENT AND TRADEMARK OFFICE
CERTIFICATE OF CORRECTION

PATENT NO. : 9,272,085 B2  
APPLICATION NO. : 13/761664  
DATED : March 1, 2016  
INVENTOR(S) : Michael R. Kurrus et al.

Page 1 of 1

It is certified that error appears in the above-identified patent and that said Letters Patent is hereby corrected as shown below:

<u>On the Title Page</u>

Left column, item (12), "Kurris et al." should be --Kurrus et al.--

Left column, item (71), Applicants: "Michael R. Kurris" should be --Michael R. Kurrus--

Left column, item (72), Inventors: "Michael R. Kurris, Ellettsville, IN (US);" should be --Michael R. Kurrus, Ellettsville, IN (US);--

Signed and Sealed this  
Third Day of May, 2016

Michelle K. Lee  
*Director of the United States Patent and Trademark Office*